United States Patent
Wolter et al.

[11] Patent Number: 5,462,746
[45] Date of Patent: Oct. 31, 1995

[54] PATCH FOR TRANSDERMAL ADMINISTRATION OF VOLATILE PHARMACEUTICALLY ACTIVE INGREDIENTS OF CHEMICALLY BASIC NATURE AND A PROCESS FOR PREPARATION

[75] Inventors: Karin Wolter, Melsbach; Walter Müller, Neuwied; Günter Simon, Hillesheim; Christa Nalbach, Leutesdorf; Hans-Rainer Hoffmann, Neuwied, all of Germany

[73] Assignee: LTS Lohmann Therapie-Systeme GmbH & Co. KG, Neuwied, Germany

[21] Appl. No.: 226,236

[22] Filed: Apr. 11, 1994

Related U.S. Application Data

[63] Continuation of Ser. No. 969,895, Nov. 2, 1992, abandoned.
[51] Int. Cl.⁶ .................................................. A61L 15/00
[52] U.S. Cl. .......................... 424/449; 424/448; 514/946
[58] Field of Search ................................ 424/449, 448; 514/946

[56] References Cited

U.S. PATENT DOCUMENTS

| | | | |
|---|---|---|---|
| 4,666,441 | 5/1987 | Andriola et al. | 424/448 |
| 4,861,800 | 8/1989 | Buyske | 514/646 |
| 4,911,707 | 3/1990 | Heiber et al. | 424/449 |
| 4,917,676 | 4/1990 | Heiber et al. | 424/449 |
| 5,120,545 | 6/1992 | Ledger | 424/449 |
| 5,242,950 | 9/1993 | Hastings | 514/654 |

FOREIGN PATENT DOCUMENTS 3643987  6/1988  Germany.

*Primary Examiner*—D. Gabrielle Phelan
*Attorney, Agent, or Firm*—Sprung Horn Kramer & Woods

[57] ABSTRACT

The invention relates to a patch for transdermal administration of volatile pharmaceutically active ingredients of chemically basic nature which comprises a multi-element system comprising (a) a matrix having distributed therein as the drug said volatile active ingredient or a physiologically acceptable salt thereof, the matrix comprising a pressure-sensitive adhesive, (b) an element of a pressure-sensitive adhesive composition which— where (a) contains a salt—contains basic groups to liberate the free base from its salt, (c) a backing layer impermeable to the diffusable ingredients of (a) and (b), and (d) a release liner impermeable to the diffusable ingredients of (a) and (b),
matrix (a) or at least a part of (b), whichever is in contact with release liner (d), having a tack sufficient for affixing the patch to the skin, any part of (b) positioned between matrix (a) and release liner (d) being permeable for the deprenyl or the salt thereof or both. The invention also relates to a process for preparing such patch and to a process for treating a patient suffering from Parkinson's or Alzheimer's disease with such patch.

27 Claims, 5 Drawing Sheets

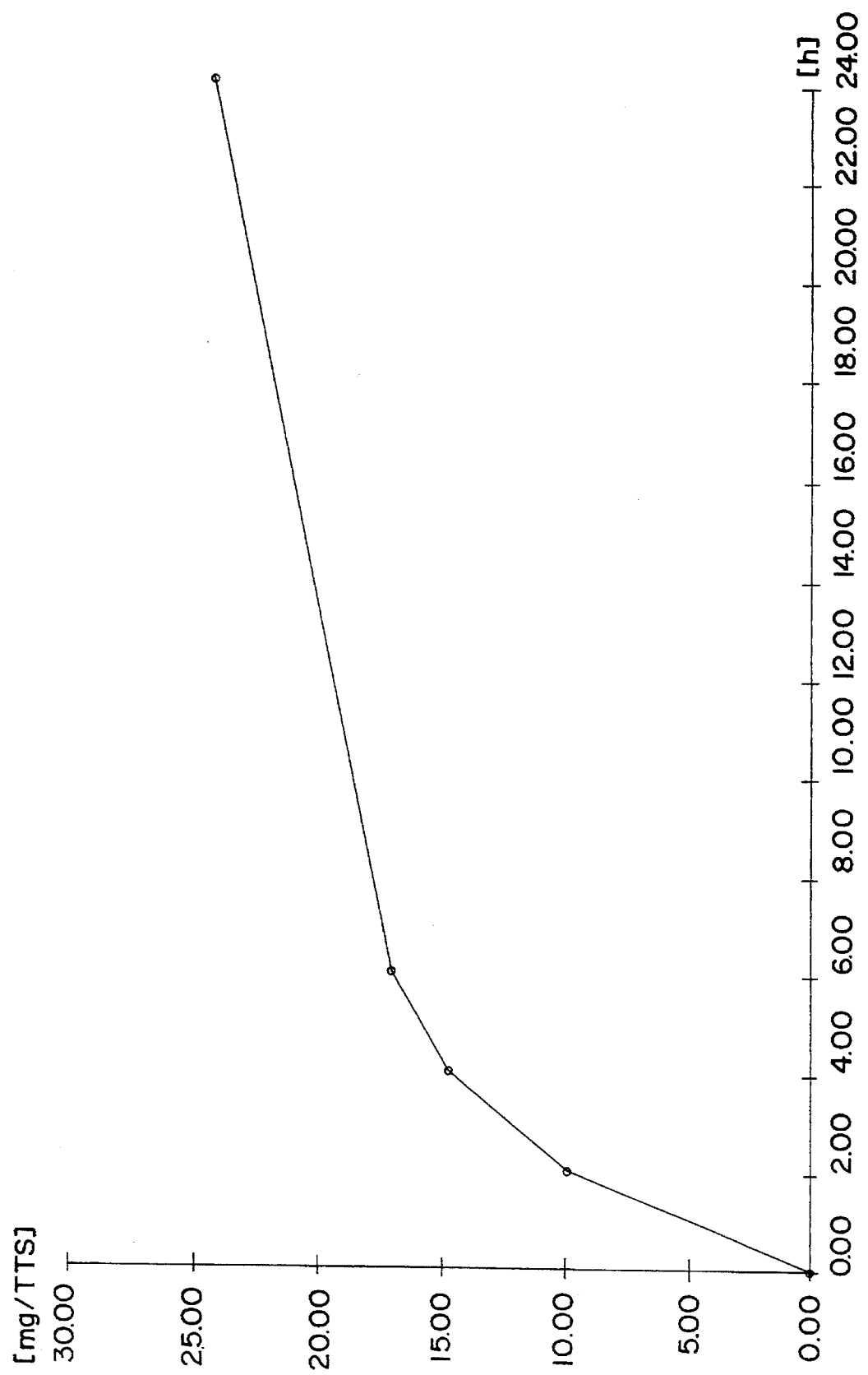

PATCH FOR TRANSDERMAL ADMINISTRATION OF VOLATILE PHARMACEUTICALLY ACTIVE INGREDIENTS OF CHEMICALLY BASIC NATURE AND A PROCESS FOR PREPARATION

This application is a continuation of application Ser. No. 07/969,895, filed Nov. 2, 1992, now abandoned.

This invention relates to a novel patch for the transdermal administration of volatile pharmaceutically active ingredients of chemically basic nature and to a process for its preparation.

A number of very valuable pharmaceutically active substances is of a chemically basic nature. Of these compounds a considerable number is volatile under ambient conditions, e.g. deprenyl, tolbuterol, propanolol, bupranolol, arecolin, verapamil, methamphetamin and amphetaminil, and particularly deprenyl (selegiline) which is a well-known compound in the treatment of Parkinson's and Alzheimer's disease.

It is known to administer deprenyl or a salt thereof orally, but it has also been proposed to administer them transdermally (cf. U.S. Pat. Nos. 4,861,800 and 4,868,218 and their European equivalent EP-OLS 406 488 and International Application WO 89/09051). Moreover, it is known from U.S. Pat. 4,812,481 (European Patent Specification 241 809) to administer selegiline together with amantadine, which combination is said to have a synergistic effect, in medicaments for oral, parenteral, rectal or vaginal administration or to the skin and mucous membranes (e.g. as solutions, lotions, emulsions, salves (ointments), plasters, etc.

It has been found in our investigations that the procedure described in International Application WO 89/09051 is in fact completely unsatisfactory and even defective. According to the example of this publication, the components are added to a solvent, such as acetone or ethanol, and mixed to give a viscous mass. This mass is then spread on top of an aluminized polyester foil (thickness 23 microns) using a conventional apparatus, to produce a film of thickness 0.2 mm when wet. The film is then said to be allowed to dry at room temperature over four to six hours.

In our investigations it has been found that in the product so produced a substantial amount of the active ingredient has been lost by evaporation so that it finally contained far less of the active ingredient than was initially employed, and the products from repeat runs varied considerably. Moreover, it is evident for those skilled in the art that from a technical and commercial point of view drying for 4 to 6 hours as according to WO 89/09051 is completely disadvantageous.

It is an object of the invention to overcome the disadvantages of the art and to provide a patch of a standardized quality for transdermal administration of deprenyl.

In general terms, the invention concerns a patch for transdermal administration of a volatile pharmaceutically active ingredient of chemically basic nature, preferably deprenyl, which comprises a multi-element system comprising (a) a matrix having distributed therein as the drug said volatile active ingredient or a physiologically acceptable salt thereof, the matrix comprising a pressure-sensitive adhesive, (b) an element of a pressure-sensitive adhesive composition which— where (a) contains a salt—contains basic groups to liberate the free base from its salt, (c) a backing layer impermeable to the diffusable ingredients of (a) and (b), and (d) a release liner impermeable to the diffusable ingredients of (a) and (b), matrix (a) or at least a part of (b), whichever is in contact with release liner (d), having a tack sufficient for affixing the patch to the skin, any part of (b) positioned between matrix (a) and release liner (d) being permeable for the active ingredient, preferably deprenyl, or the salt thereof or both.

In the process of manufacturing the patch of the invention, element (a) is maintained, until processing with element (b), under conditions such that the salt does not suffer decomposition and any layer of (b) positioned between element (a) and release liner (d) being permeable for the drug.

In a specific embodiment the invention is also concerned with a process for preparing a patch according to claim 1 which comprises (i) forming a mixture of a physiologically acceptable salt of a volatile pharmaceutically active ingredient and a fluid composition of a pressure-sensitive adhesive material with a solvent or diluent, and evaporating the solvent or diluent from this mixture to produce a matrix (a) of a homogeneous substrate in layer or particulate form, (ii) forming a fluid composition containing a solvent or a diluent and said pressure-sensitive adhesive composition which may contain basic groups suitable for the formation of the free base from its salt, stratifying the adhesive composition to at least one layer which may have a hole section of a defined geometrical shape, and evaporating the solvent or diluent from such layer, to form layer (b), (iii) laminating matrix (a) with layer (b), (iv) applying said backing layer (c) and said release liner (d) to matrix (a) and layer (b) such that either matrix (a) or a layer of (b) permeable for the free base is in direct contact with the release liner (d), the matrix (a) loaded with the active ingredient and at least one layer (b) having a tack sufficient for affixing the patch to the skin, matrix (a) being maintained, until processing with composition (b), under conditions such that said salt does not suffer decomposition, and process steps (i) and (ii) being carried out in any desired order. A further object of the invention consists in a process for treating a patient suffering from Parkinson's or Alzheimer's disease which comprises treating such patient with a patch as defined herein-before.

Suitable drugs to be processed in the patches of the invention are, for example, tolbuterol, propanolol, arecolin, verapamil, methamphetamin, amphetaminil and preferably deprenyl, and other compounds well-known to those skilled in the art.

The matrix (a) initially or after storing may also include the free base instead of or in addition to the salt, but it is preferred that initially at least some of the active ingredient, preferably the whole amount thereof, is provided in the form of a physiologically acceptable salt, e.g. a mineral acid salt such as the sulfate, phosphate, but especially a hydrogen halide salt and more particularly the hydrochloride or hydrobromide. Where a salt is used, its diffusion ability may be improved by the concomitant use of a conventional solubilizer, such as glycerol, 1,2-propanediol, the monomethyl or monoethyl ether of diethylene glycol, 2-octyldodecanol, the laurate, palmitate, stearate or oleate of sorbitol, $C_8/C_{10}$ ethoxylated glycerides, and ethoxylated oleic glycerides.

The drug may be contained in its free (base) form in element (b) alone or in addition to matrix (a). Element (b) can be formed of an amino-containing polymerizable monomer or of a mixture of an adhesive polymer and a base or a combination thereof. A suitable base is a non-volatile amine, such as aminoalcohols, for example mono- and diethanol amine, particularly, however, an amino-containing polymer. The basic groups of (b) serve to liberate the free base from layer (a) eventually.

Element (b) may comprise a single layer or multiple, in particular 2 to 3, layers, one or more of which are basic. Element (b) may also be shaped in a circular form, surrounding matrix (a) and possibly also covering it to the side of the backing layer. In other words, matrix (a) may be surrounded to all but one side by element (b), the remaining side being destined for attaching to the skin with the aid of the tack activity of element (a). Advantageously, however, matrix (a) is laminated between two layers of (b). In a preferred embodiment, however, one layer (b) is on one side of matrix (a) and another layer (b) is on the other side of matrix (a). In such event, that layer (b) which is closer to release liner (d) has often a greater tack and a lower amine content than that layer (b) which is more remote from release liner (d). In a preferred embodiment, element (b) is in direct contact with release liner (d).

When the active ingredient is deprenyl, it is advantageously in the L-form. It is generally present in about 5 to 75, preferably about 10 to 50, mg per patch, calculated as the free base, the patch ranging in size from about 10 to 25, preferably about 12 to 20, cm$^2$. The amounts of the other active ingredients are dependent on their effective doses, but can also vary within broad limits, e.g. in the same as indicated herein-before.

The element (b) may additionally contain ingredients to enhance the permeation, distribution and/or penetration of the active materials. Suitable permeation enhancers are the compounds mentioned here-before as solvents, but in addition also other conventional enhancers may be used, such as esters of the formula $[CH_3(CH_2)_mCOO]_nR$ in which m is an integer from 8 to 16, preferably from 8 to 12; n is 1 or 2, preferably 1; and R is a lower alkyl ($C_1$–$C_3$) residue which may be substituted with up to 2 hydroxyl groups, or a mixture of such an ester or methyl laurate and diethylene glycol monomethyl or monoethyl ether. The preferred esters are lower alkyl ($C_1$–$C_3$) esters of lauric acid, such as propylene glycol monolaurate (PGML). Other suitable enhancers are lauric acid, capric acid, oleic acid, glycerol oleate, higher alcohols, such as dodecanol, undecanol, octanol, esters of carboxylic acids in which the alcohol component may be a polyethoxylated alcohol, diesters of dicarboxylic acids, such as di-n-butyladipate, and triglycerides, particularly medium-chain triglycerides of the caprylic/capric acids, or coconut oil, polyhydric aclohols, for example, glycerol and 1,2-propanediol which are etherified by polyethylene glycols.

Elements (a) and/or (b) may further contain additional active ingredients, e.g. amantadine together with deprenyl, and/or other substances such as coloring, flavoring and preserving agents, fillers, etc.

The arrangement of elements (a) and (b) can vary significantly. In a preferred aspect element (b) is in direct contact with backing layer (c). Layer (c) and/or release liner (d) can comprise a polyester foil which may be aluminized, or an aluminized foil of a synthetic resin, such as polypropylene, nylon, polycaprolactame or silicone foil.

The overall patch may range in weight from about 0.05 or 10, preferably about 0.1 to 5 grams, and in thickness from about 0.1 to 10, preferably about 0.5 to 5 mm.

BRIEF DESCRIPTION OF THE DRAWINGS

The invention will be further described with reference to the accompanying drawings, wherein:

FIG. 10 shows a graph of the in vitro-release according to the well-known rotating cylinder method of the tempered patches as shown in FIG. 1.

Figure 1:
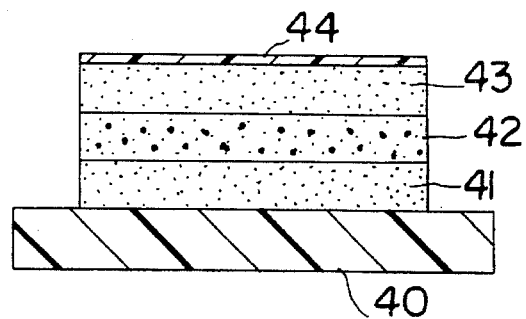
FIG. 1 is a cross-section through one embodiment of a patch in accordance with the present invention.

Referring now more particularly to the drawings, in FIG. 1 there is shown a patch in accordance with the present invention comprising a removable release liner 40 to which there adheres layer 41 of element (b), initially free of active material. To layer 41 there is adhered a layer 42 of matrix (a) containing the active material in salt form. That in turn carries an adhesive layer 43 of element (b) which is adhered to an impenetrable backing layer (c) 44.

Figure 2:
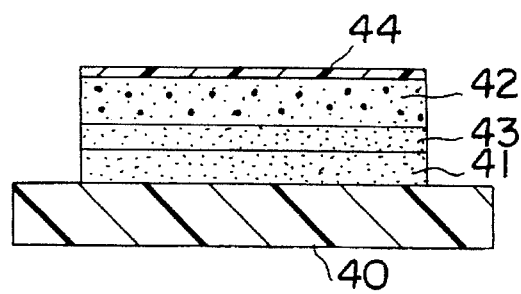
FIG. 2 is a cross-section through another embodiment of a patch in accordance with the present invention.

In the variation of FIG. 2, the layers 42 of matrix (a) and 43 of element (b) have been switched but it is necessary that 42 adhere to backing layer 44 either by its inherent adhesiveness or an added adhesive (not shown).

Figure 5:
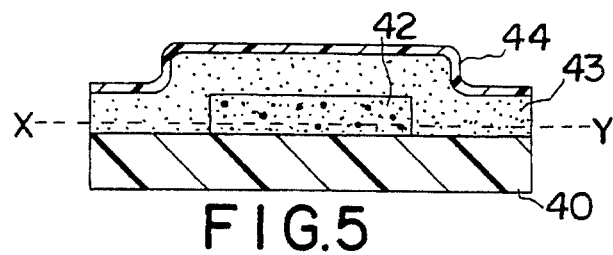
FIG. 5 is a cross-section through a further embodiment of a patch in accordance with the present invention in which element (b) surrounds matrix (a) and covers it to the side of the backing layer.
Figure 6:
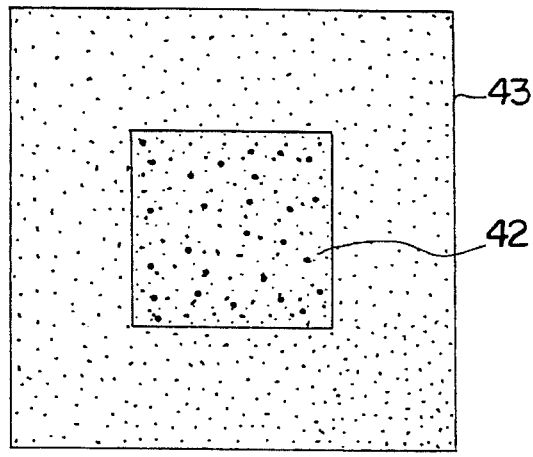
FIG. 6 shows a plan view of the patch along the line between X and Y in FIG. 5.

In the variation of FIG. 5 to 9, element (b) covers matrix (a) to the side of the backing layer, although matrix (a) could be in direct contact with the backing layer also. It is an inherent feature in this embodiment that a part of element (b) sufficient for a satisfactory adhesion to the skin surrounds matrix (a). Matrix (a) may be shaped as shown in FIG. 6 or in any of FIG. 9B–J, (the shape of FIG. 9A being identical with that in FIG. 6)

The invention will be further described in the following illustrative examples.

EXAMPLE 1

1.1 A solvent-based non-crosslinking acrylic based pressure-sensitive adhesive soluble in ethyl acetate (sold under the trademark DURO-TAK 280-2287) having a solids content of 50–52% and a viscosity of 10,000–24,000 mPa s at 25° C. is dissolved in a concentration of 50% by weight in ethyl acetate. 800 grams of such solution are combined with 2000 grams of deprenyl hydrochloride and 3700 grams of ethyl acetate, forming a dispersion. An additional about 7200 grams of the acrylate polymer solution are added to the dispersion, while stirring and heating, and about 1400 grams of ethyl acetate are then evaporated.

1.2 Separately 3200 grams of a copolymer of dimethylaminoethyl methacrylate and neutral methacrylic acid esters (sold under the tradename Eudragit E), e.g. esters of alkyl alcohols of 1 to 4 carbon atoms such as methyl, ethyl, and isopropyl, the various butyls (n-, sec-, iso-, tert-) and hexyl are dissolved in 3200 grams of methyl ethyl ketone. Then there are added 22,800 grams of a self-crosslinking, acrylic based pressure-sensitive adhesive (sold under the tradename DURO-TAK 280-2516) having a solids content of 41–43% in a solvent blend of 64% ethyl acetate, 25% ethanol, 9% heptane and 2% methanol a viscosity of 3,000 to 7,000 mPa s at 25° C.

1.3 The solution of (1.2) is coated onto a first removable foil and the solvent evaporated to leave 64 grams/m² of solids. The coated face of the first foil is placed onto a 15μ thick polyester backing layer (c).

1.4 Separately, the dispersion of 1.1 is coated onto a second removable foil in an amount containing 62 grams/m² of non-volatile material. The solvent is evaporated. The coating of the second foil is laminated onto the coated face of polyester backing layer (c) after removal of the first foil from the product of (1.3). The intermediate at this stage comprises a polyester backing layer, a deprenyl free basic polymer layer, a deprenyl-containing polymer layer and the temporary second foil.

1.5 The solution of (1.2) is coated onto a release liner (200 micron thick polyester) to leave 64 grams/m² of non-volatiles. After evaporation of the volatiles, onto the residual material there is placed a third removable foil.

1.6 The temporary second foil of (1.4) and a third foil of (1.5) are removed and the residual materials laminated. The resulting product is as shown in FIG. 1.

The product is cut into individual patches of 41×41 mm and packaged. They are suitable for administration after some weeks' storage, which duration is dependent on the storage temperature applied. Such products are highly uniform and contain substantially all the active material initially applied.

Figure 3:
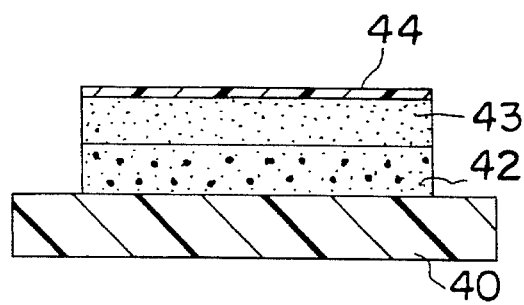
FIG. 3 is a cross-section through a further embodiment of a patch in accordance with the present invention in which element (b) is positioned adjacent to the backing layer and the matrix (a) is situated between element (b) and the release liner.
Figure 4:
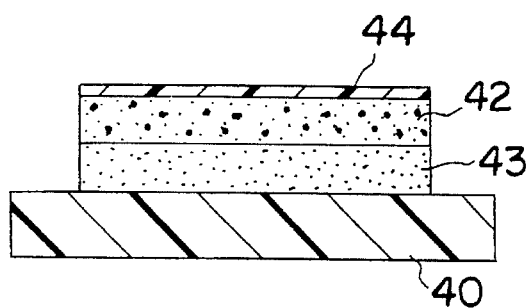
FIG. 4 is a cross-section through a further embodiment of a patch in accordance with the present invention in which the position of element (b) and matrix (a) are exchanged vice versa compared with FIG. 3.

In generally similar fashion the product of FIG. 2, 3 and 4 can be made.

Products as shown in FIG. 3 and 4 can be made as follows: The two layers 42 and 43 are manufactured in a similar fashion as those in FIG. 1 and 2 and the system is then further processed as described with regard to FIG. 1.

Figure 7:
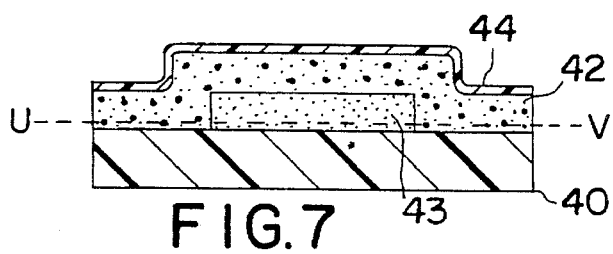
FIG. 7 and 8 show embodiments like those in FIG. 5 and 6, but in which the positions of matrix (a) and element (b) are exchanged vice versa.
Figure 8:
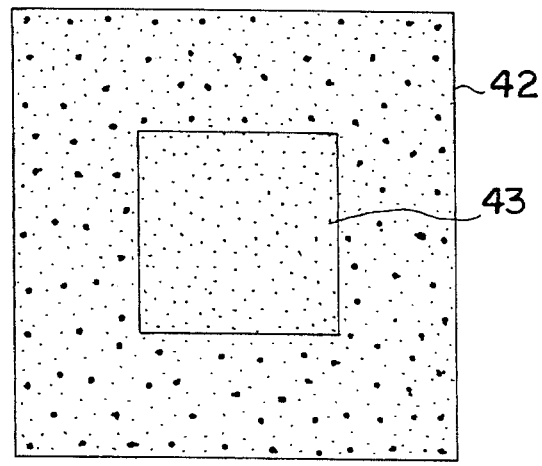
Figure 9A:
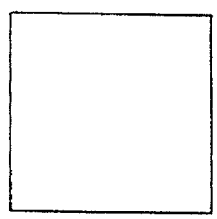
FIG. 9 shows various plan views of the matrix portion of FIG. 5 along the line between X and Y and of the element (b) portion of FIG. 7, respectively.
Figure 9B:
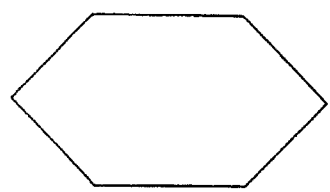
Figure 9C:
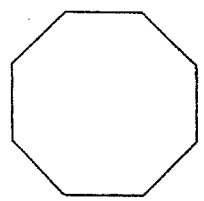
Figure 9D:
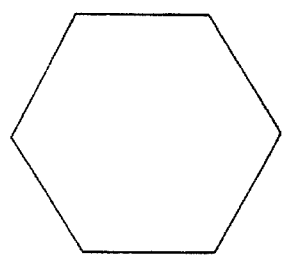
Figure 9E:
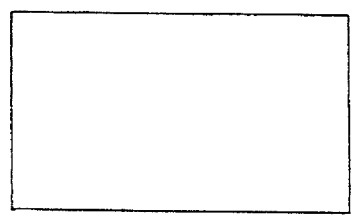
Figure 9F:
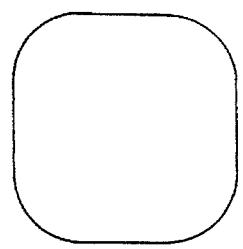
Figure 9G:
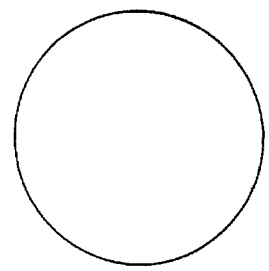
Figure 9H:
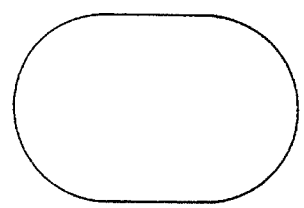
Figure 9I:
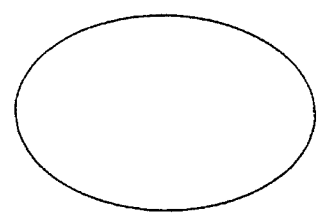
Figure 9J:
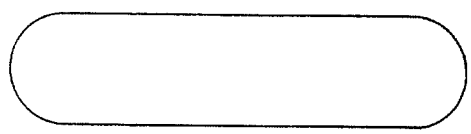
Figure 11:
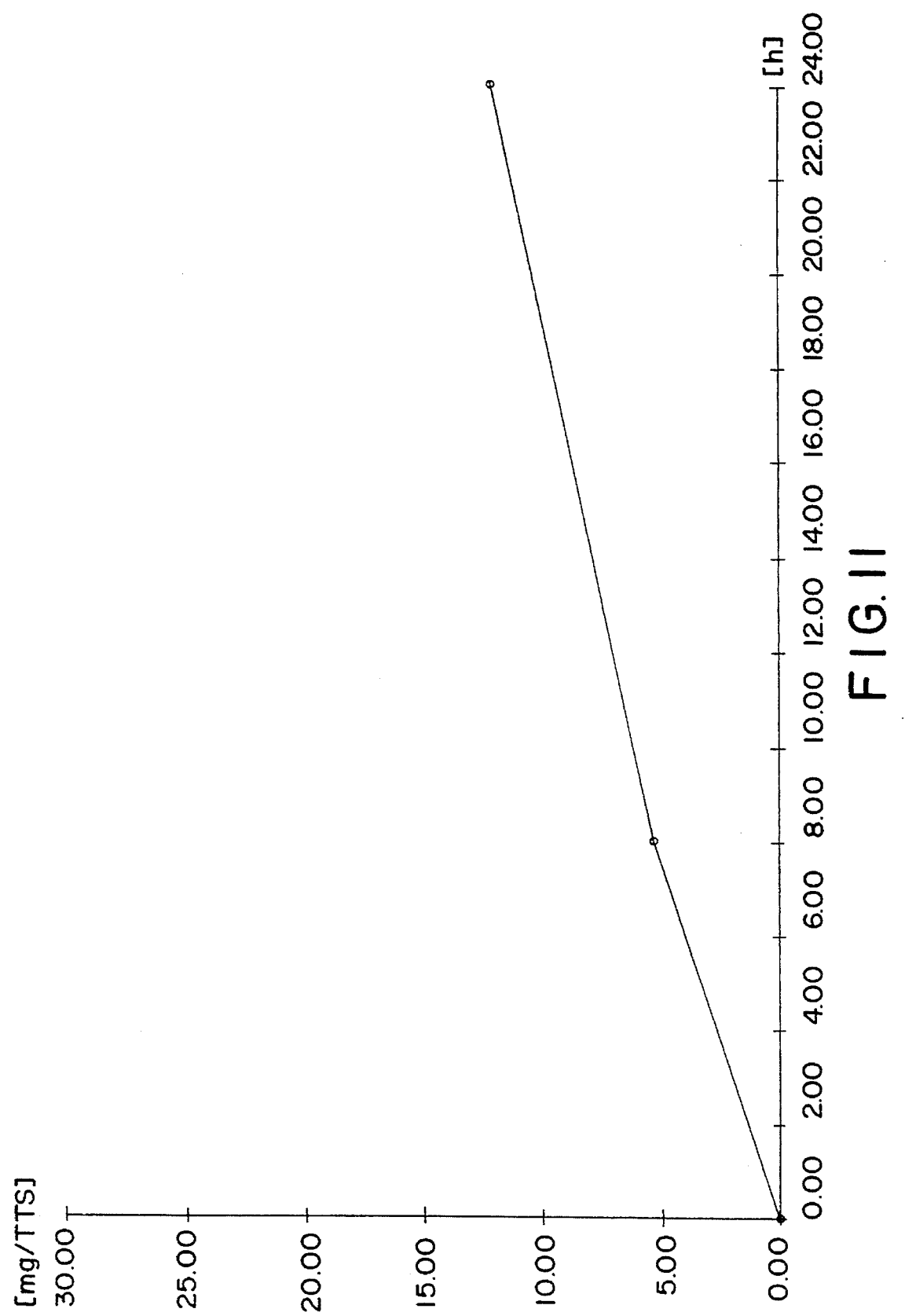
FIG. 11 shows a graph of the in vitro-mouse skin-penetration of the tempered patches as shown in FIG. 1. Graphs of FIG. 10 and 11 both represent the average results of three experiments.

Products according to FIG. 5 and 7 can be prepared in a similar manner as described with regard to FIG. 3 and 4. However, the two layers will be combined such that in the embodiment of FIG. 5 the drug-loaded matrix and in the embodiment according to FIG. 7 the pressure-sensitive adhesive element (b) is punched in any of the geometrical forms of FIG. 9A–J, and the resulting product is then laminated in the case of FIG. 5 with a pressure-sensitive adhesive element (b) and in the case of FIG. 7 with the matrix (a).

It will be appreciated that the instant specification and claims are set forth by way of illustration and not limitation, and that various modifications and changes may be made without departing from the spirit and scope of the present invention.

We claim:

1. A patch for transdermal administration of volatile pharmaceutically active ingredients having a chemically basic nature, said patch comprising the following layers:

(a) a pressure-sensitive adhesive composition having distributed therein a physiologically acceptable salt of said volatile active ingredient;

(b) a pressure-sensitive adhesive composition having distributed therein an amino-group-containing compound to liberate the free base from said salt, said pressure-sensitive adhesive composition being identical to or different from the pressure-sensitive adhesive composition in (a);

(c) a backing layer impermeable to diffusable ingredients of (a) and (b); and (d) a release liner impermeable to diffusable ingredients of (a) and (b);

wherein:

(i) layer (a) or layer (b), whichever is in contact with layer (d), having a tack sufficient for affixing the patch to the skin;

(ii) any part of layer (b) positioned between layer (a) and layer (d) being permeable to the volatile active ingredient and the salt thereof; and (iii) layer (a) and layer (b) being laminated to one another and, at the time of lamination, said salt being contained only in layer (a) and said amino-group-containing compound being contained only in layer (b).

2. A patch according to claim 1, wherein the salt comprises the hydrochloride or the hydrobromide or both.

3. A patch according to claim 1, in which (a) contains a solubilizer for the physiologically acceptable salt.

4. A patch according to claim 1, wherein the active ingredient is deprenyl.

5. A patch according to claim 4, wherein the deprenyl is the L-form.

6. A patch according to claim 1, wherein (b) comprises an adhesive polymer in which there is distributed a non-volatile amine.

7. A patch according to claim 1, wherein (b) comprises a plurality of layers, at least one of which contains the amino-group-containing compound.

8. A patch according to claim 7, wherein (b) consists of 2 to 3 layers.

9. A patch according to claim 1, wherein (a) is surrounded to all but one side by (b), the remaining side being destined for attaching to the skin with the aid of the tack activity of (a).

10. A patch according to claim 1, wherein (a) is surrounded by (b) such that (a) is in direct contact with backing layer (c).

11. A patch according to claim 1, wherein (a) is laminated between 2 layers of (b).

12. A patch according to claim 11, wherein of the two layers of (b) a layer $B_1$ is positioned on release liner (d) and a layer $B_2$ on backing layer (c), layer $B_1$ having greater tack activity than layer $B_2$.

13. A patch according to claim 12, wherein that layer (b) which is closer to release liner (d) has a lower content of amino groups than that layer (b) which is more remote from (d).

14. A patch according to claim 12, wherein (a) is positioned between layers $B_1$ and $B_2$.

15. A patch according to claim 1, wherein (b) includes a polymer containing the amino groups to liberate the free base from the salt.

16. A patch according to claim 1, wherein (b) is in direct contact with release liner (d).

17. A patch according to claim 1, wherein (b) further includes a permeation enhancer.

18. A patch according to claim 1, wherein at least one of the backing layer (c) and the release liner (d) comprises a polyester foil.

19. A patch according to claim 1, wherein at least one of the backing layer (c) and the release liner (d) comprises an aluminized foil of a synthetic resin.

20. A patch according to claim 4, wherein the deprenyl component is present in an amount of from about 5 to about 75 mg, calculated as deprenyl base.

21. A patch according to claim 1, wherein the size of the patch where it is destined to contact the skin, is from about 10 to about 25 cm$^2$.

22. A process for preparing a patch according to claim 1 which comprises
   (i) forming a mixture of a physiologically acceptable salt of a volatile pharmaceutically active ingredient and a fluid composition of a pressure-sensitive adhesive material with a solvent or diluent, and evaporating the solvent or diluent from this mixture to produce a matrix (a) of a homogeneous substrate in layer or particulate form,
   (ii) forming a fluid composition containing a solvent or a diluent and said pressure-sensitive adhesive composition which may contain amino groups suitable for the formation of the free base from its salt, stratifying the adhesive composition to at least one layer which may have a hole section of a defined geometrical shape, and evaporating the solvent or diluent from such layer, to form layer (b),
   (iii) laminating (a) with layer (b),
   (iv) applying said backing layer (c) and said release liner (d) to matrix (a) and layer (b) such that either matrix (a) or a layer of (b) permeable for the free base is in direct contact with release liner (d), matrix (a) loaded with the active ingredient and at least one layer (b) having a tack sufficient for affixing the patch to the skin, matrix (a) being maintained, until processing with composition (b), under conditions such that said salt does not suffer decomposition, and process steps (i) and (ii) being carried out in any desired order.

23. A patch according to claim 6, wherein the non-volatile amine is an aminoalcohol.

24. A patch according to claim 23, wherein the aminoalcohol is selected from the group consisting of monoethanolamine and diethanolamine.

25. A patch according to claim 1, wherein the pressure-sensitive adhesive composition of (a) or (b) or both comprises a solvent based acrylic-based pressure-sensitive adhesive.

26. A patch according to claim 1, wherein the pressure-sensitive adhesive composition (b) contains as an additional ingredient a copolymer of dimethylaminoethylmethacrylate and neutral methacrylic acid ester, the alcohol component of which has from 1 to 6 carbon atoms.

27. A patch according to claim 1, wherein (a) or (b) or both additionally contain active ingredient in the form of the free base.

* * * * *